(12) United States Patent
Copeland

(10) Patent No.: US 11,020,124 B1
(45) Date of Patent: Jun. 1, 2021

(54) LEFT ATRIAL APPENDAGE CLOSURE DEVICE AND METHOD

(71) Applicant: Henry Copeland, Montgomery, AL (US)

(72) Inventor: Henry Copeland, Montgomery, AL (US)

( * ) Notice: Subject to any disclaimer, the term of this patent is extended or adjusted under 35 U.S.C. 154(b) by 104 days.

(21) Appl. No.: 16/207,638

(22) Filed: Dec. 3, 2018

Related U.S. Application Data

(60) Provisional application No. 62/694,106, filed on Jul. 5, 2018.

(51) Int. Cl.
*A61B 17/12* (2006.01)
*A61B 17/00* (2006.01)

(52) U.S. Cl.
CPC .. *A61B 17/12122* (2013.01); *A61B 17/12031* (2013.01); *A61B 17/12131* (2013.01); *A61B 2017/00407* (2013.01); *A61B 2017/00477* (2013.01); *A61B 2017/00526* (2013.01); *A61B 2017/00862* (2013.01); *A61B 2017/1205* (2013.01)

(58) Field of Classification Search
CPC ............. A61M 25/04; A61B 17/12104; A61B 17/12022; A61B 17/12027; A61B 17/12122; A61B 17/12031; A61B 17/12131; A61B 17/12095; A61B 17/1205; A61F 6/146
See application file for complete search history.

(56) References Cited

U.S. PATENT DOCUMENTS

| | | | |
|---|---|---|---|
| 3,874,388 A * | 4/1975 | King ................... | A61B 17/0057 606/232 |
| 4,007,743 A * | 2/1977 | Blake ................. | A61B 17/0057 606/232 |
| 9,592,058 B2 | 3/2017 | Erzberger et al. | |
| 9,808,253 B2 | 11/2017 | Li | |
| 9,901,350 B2 | 2/2018 | McGuckin | |
| 10,052,168 B2 | 8/2018 | Krishnan | |
| 2011/0082495 A1 * | 4/2011 | Ruiz ................... | A61B 17/0057 606/213 |
| 2017/0156904 A1 * | 6/2017 | Liu .......................... | A61F 2/02 |
| 2017/0231639 A1 * | 8/2017 | Miller .................. | A61B 17/122 606/195 |

* cited by examiner

*Primary Examiner* — Wade Miles
*Assistant Examiner* — Mohammed S Adam
(74) *Attorney, Agent, or Firm* — Walter A. Rodgers

(57) ABSTRACT

A device to close the left atrial appendage of a patient including a hollow shell having opposed male and female ratchet latches with the shell moveable into the left atrial appendage orifice to close the orifice by interconnecting the latches to expand the shell in conformance with the profile of the orifice.

17 Claims, 21 Drawing Sheets

LEFT ATRIAL APPENDAGE CLOSURE DEVICE AND METHOD

The benefits under 35 USC 119 are claimed of provisional patent application 62/694,106 filed Jul. 5, 2018.

BACKGROUND OF THE INVENTION

This invention pertains to the field of implanted medical devices, particularly those implanted in the human heart. The Left Atrial Appendage (LAA) is a portion of the left atrium of the heart, being approximately one quarter or less in volume of the left atrium. The LAA is connected to left atrium via a passage or orifice providing for free flow of blood between the atrium and the appendage. As the heart beats, expansion and contraction of the atrium causes blood flow into and out of the LAA chamber.

An abnormal heartbeat, in particular that marked by pauses, skips or delays in the flow of blood into and out of the LAA causes blood to stagnate therein. Clotting agents in the blood instantaneously form microscopic size particles in the stagnant blood. Such particles of clotted blood accumulate and settle in the LAA chamber from which they can be caught up in the blood flow and carried downstream to points of blood flow restriction. At such points of restriction, clotted blood particles may block vital blood flow thereby causing damage to body tissue.

This invention provides a device which will, when installed in the appendage orifice, seal off and block blood flow into and out of the appendage chamber. Installation of such devices now in use in the industry is typically performed in a catherization setting using a standard transseptal procedure. By closing off the LAA, the risk of tissue damage by the blockage of blood flow by clotted particles is greatly reduced.

Devices are known to exist that effect sealing of the appendage chamber from the atrium and this invention in several ways improves known sealing procedures. One of the greatest safety concerns with the LAA occlusion or manipulation of any device in the the LAA is the possibility of perforation. The LAA is highly heterogeneous and as thin as one millimeter at many points. Great care must be taken for safe delivery of a closure device. This is important in highly experienced hands and is even more important in the hands of a new surgeon. The present invention in several ways lessens the possibility of perforation.

After deployment of the closure device in the LAA, endothelialization, the growth of surrounding human tissue, will engulf such device and provide permanent closure of the LAA. To be useful in the long term an LAA device must undergo this process and provide for such growth. This invention provides a surface receptive to and supportive of endothelialization.

BRIEF SUMMARY OF THE INVENTION

The device, according to this invention, is constructed of a material amenable to creation, during the manufacturing process, of a modified surface texture in a certain exposed area. Such surface texture being receptive to and supportive of endothelialization. The construction creates an area of textured surface for that section of the device body which, upon deployment and final placement, remains exposed in the atrium chamber. Such area extending over the exposed face to achieve intimate contact with the atrium wall surrounding the orifice provides an unobstructed and receptive path for the endothelialization process.

The device is constructed of a pliable plastic material which, by exertion of correct forces applied at critical points on the device surface during deployment, is readily urged to conform to the unfilled LAA orifice profile without harsh metallic contact with soft heart tissues. This provides for adjustment of the device for close fitting to the LAA orifice at the time of installation. Existing LAA devices may require complete insertion into and extraction from the atrium for measurement and correct sizing.

The device, at the time of expansion, provides a wider latitude in correct initial placement relative to the LAA orifice than existing devices. Expansion and deformation of the device body creates opposed end flanges which aid in its location to straddle the LAA orifice. Upon final placement, expanded end flanges provide for a secure and permanent location of the device.

The device will, when deployed in the orifice of the LAA and expanded to contact the orifice wall, comply closely in shape and contour to form a positive seal between device and the orifice wall and will diametrically expand its opposed end sections to a diameter greater than its middle section, thus being retained in the orifice and secured from dislodging.

The device is safer than existing units by providing a mechanism comprising few elements which may damage body tissue and is constructed of a highly compliant, low durometer material, which allows incidental inadvertent contact without damage to body tissue.

The device also is safer than existing units by providing a greater margin of error in the radial alignment of the device relative to the LAA orifice at the time of deployment and by providing a unit which, at the time of deployment, allows a greater margin of error in the longitudinal position of the closure device relative to the LAA orifice and by providing a unit which includes an improved training environment for new surgeons. The device also is safer than existing units by providing a device which allows total retraction of unit from the LAA orifice at any time during deployment and prior to final placement of the device.

TABLE OF REFERENCE NUMERALS

Figure 1:
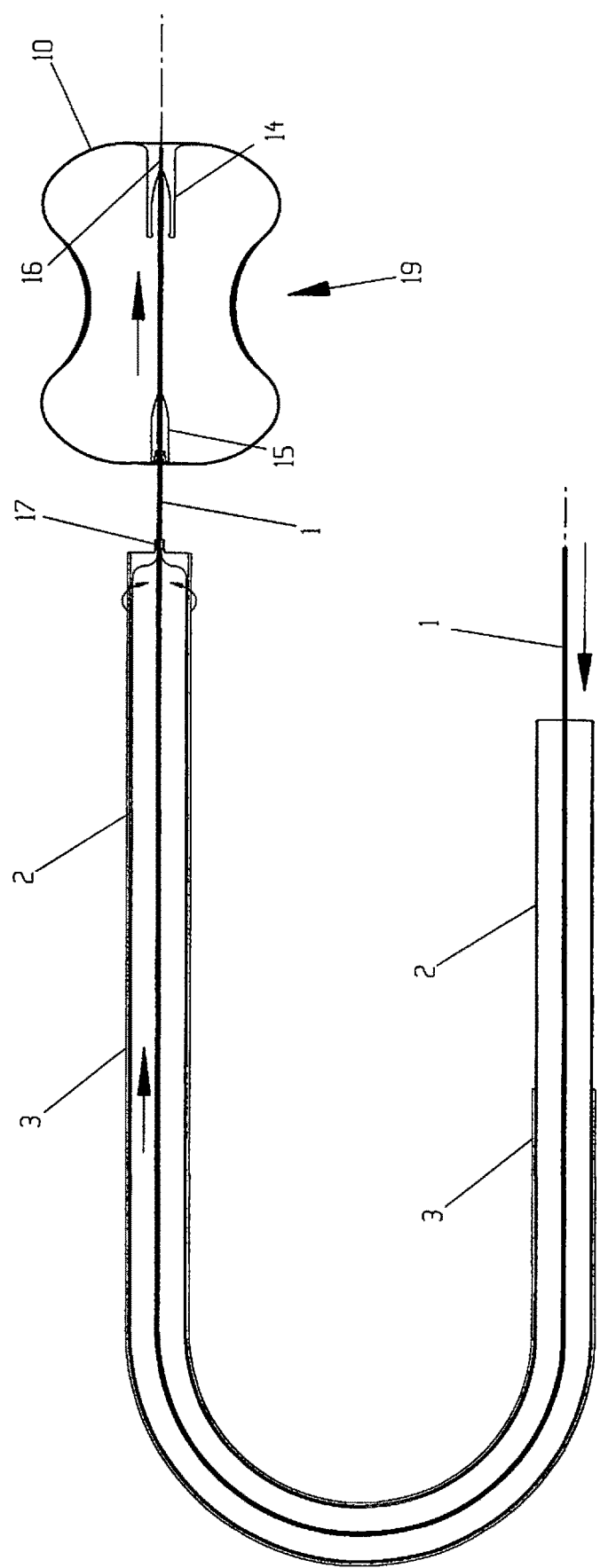
FIG. 1 is a top plan view of the left atrial appendage device according to this invention.

1. Wire
2. Inner sheath
3. Outer sheath
4. Inferior vena cava

5. Right ventricle
6. Right atrium
7. Interatrial septum
8. Left atrium
9. Left atrial appendage
10. Shell
11. Left ventricle
12. Oriface
13. Reinforced body area
14. Ratchet latch female
15. Ratchet latch male
16. Wire connect threads
17. Inner sheath connect threads
18. Close flap
19. Device
20. Latch pawl
21. Latch ridges
22. Slot
23. Flap cavity

DETAILED DESCRIPTION OF THE INVENTION

In the drawings, the numeral 19 designates the left atrial appendage device according to this invention. FIG. 1 is a cross-sectional view of device 19 and related elements which comprises shell 10, ratchet latch female 14, ratchet latch male 15, wire connect threads 16, inner sheath connect threads 17, inner sheath 2, outer sheath 3 and wire 1. In operation, outer sheath 3 and inner sheath 2 are manipulated longitudinally and radially at the proximate ends thereof manually as is well known. Wire 1, contained within inner sheath 2, is likewise manually manipulated longitudinally and radially.

Figure 2:
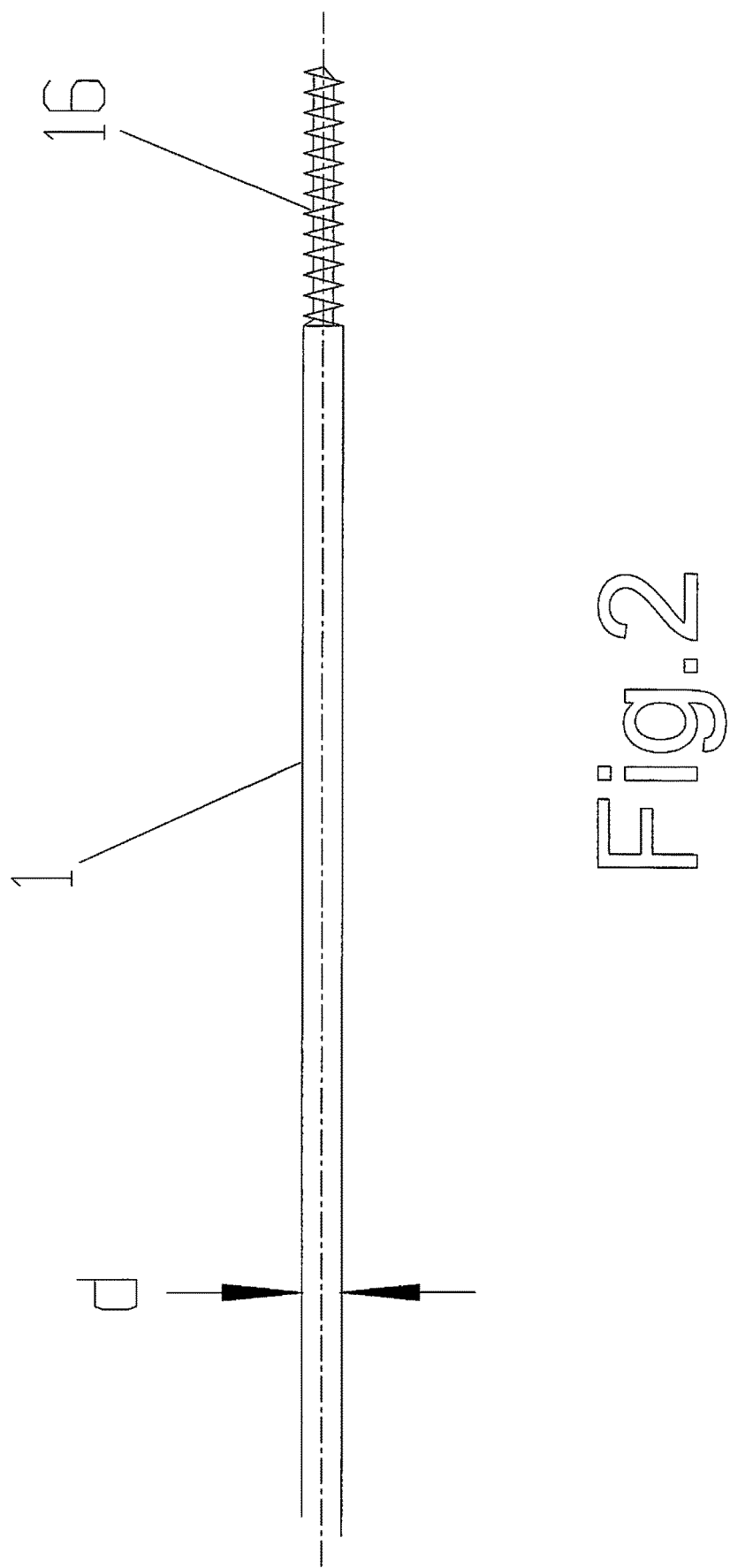
FIG. 2 is an enlarged view of the wire element.

FIG. 2 shows wire 1 which is constructed of an alloy and selected for the required properties of stiffness, durability, surface finish, machinability and chemical neutrality. Wire 1 is round in cross-section with a diameter of 0.001 to 0.090 inches and threaded at its distal end for attachment to shell 10 by means of wire connect threads 16.

Figure 3:
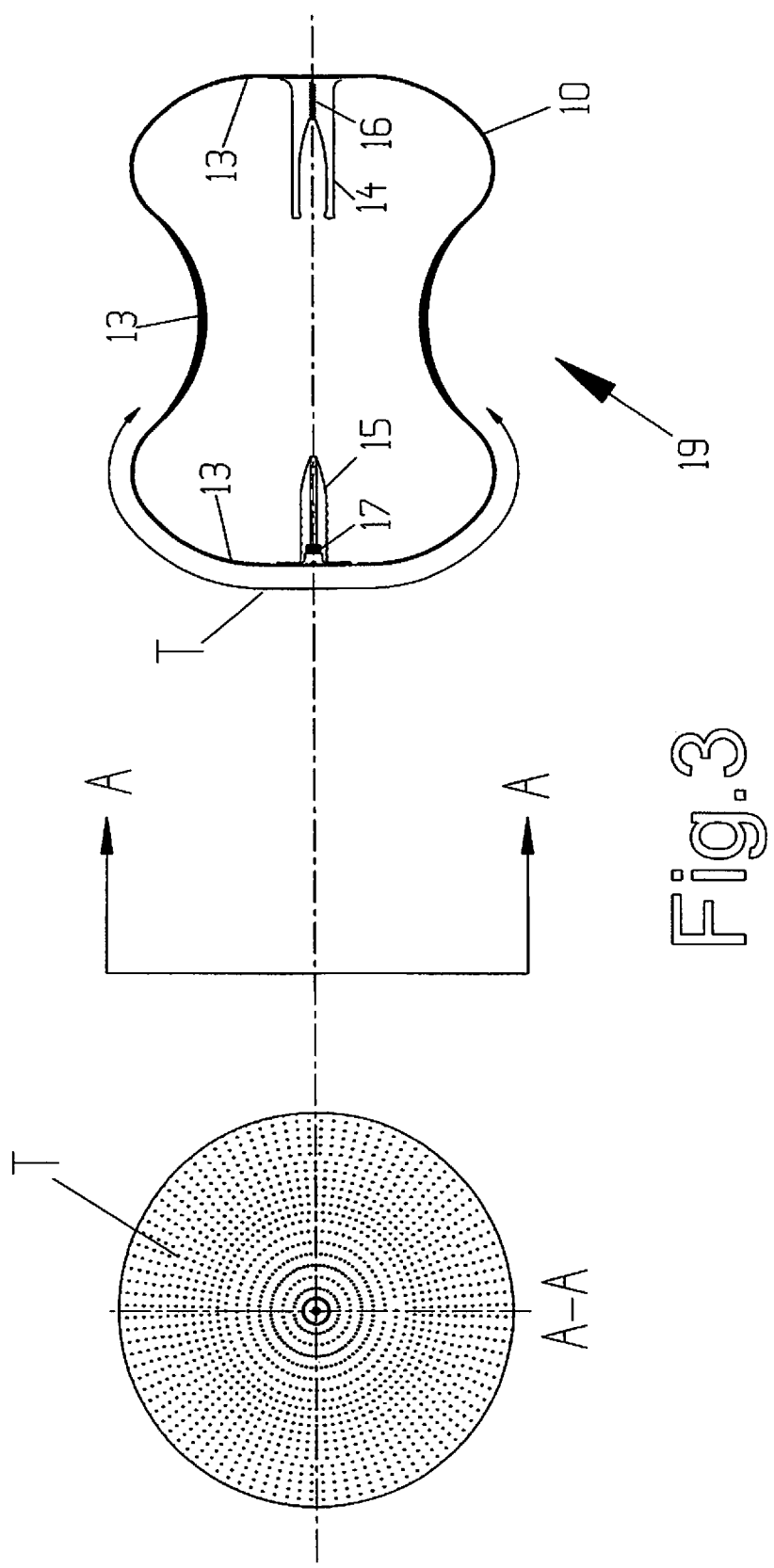
FIG. 3 is an enlarged view of the shell feature.

FIG. 3 illustrates shell 10 which is generally spherical in shape and fabricated from a plastic material compound exhibiting qualities of strength, elasticity, printability and compatibility with the required application such as a thermoplastic elastomer (TPE). Shell 10 is typically one integral unit made by the use of a 3-D printing process well known in the industry. Shell 10 is provided with a reduced circumference at an area equidistant from its polar ends.

Ratchet latch female 14 and ratchet latch male 15 are located at the respective polar ends of shell 10. Also, the end walls at the bases of ratchet latch female 14 and ratchet latch male 15 are stiffened. Reinforced body area 13, generated by buildup of shell 10 material during fabrication, offers increased resistance to stretching and retains reduced circumference as the stiffened polar ends of device 19 are urged toward a connection. The reduced circumference in the mid-waist area creates a spool like profile in shell 10 which is useful in positioning and retaining shell 10 in the mouth of LAA orifice 12. Cross-section A-A in FIG. 3 illustrates surface texture T imparted to the area by the manufacturing process and of an engineered design which is receptive to and supportive of endothelialization.

Figure 4:
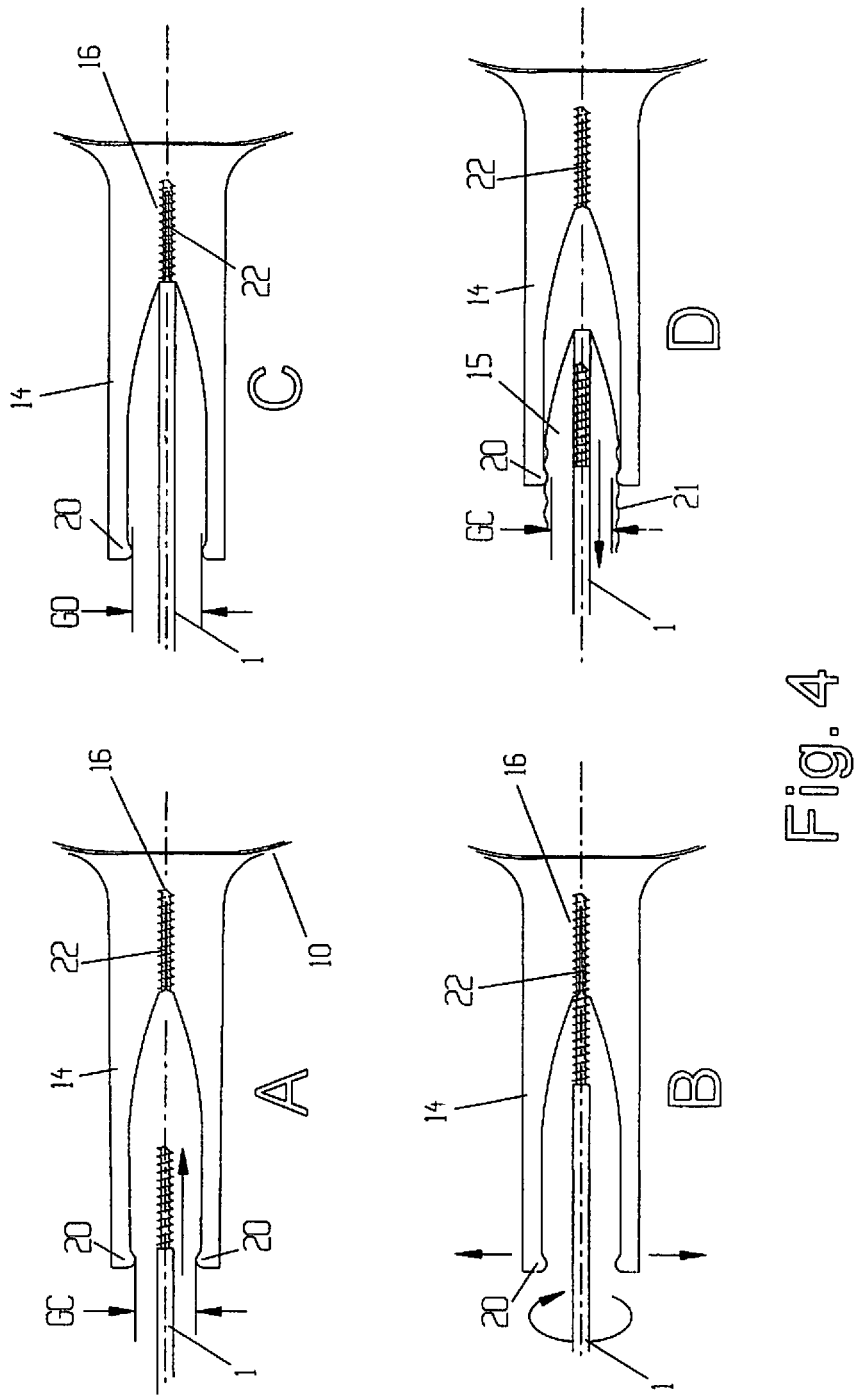
FIGS. 4A,B,C,D depict details of the ratchet latch female feature.

FIG. 4 illustrates ratchet latch female 14 which is an integral part of shell 10. Ratchet latch female 14 is divided into similar halves each sharing wire connect threads 16 with the halves separated by slot 22. The construction of ratchet latch female 14 causes latch pawls 20 to assume a natural molded shape shown in FIG. 4A thereby creating closed gap GC around ratchet latch male 15.

As illustrated in FIG. 4B, insertion and rotation of wire 1 caused wire connect threads 16 of ratchet latch female 14 to engage the mouth of slot 22 and wedge slot 22 open thereby spreading apart latch pawls 20. Fully engaged wire 1, as shown in FIG. 4C, provides maximum open gap GO and limited slight closing force of latch pawls 20 upon latch ridges 21 formed on ratchet latch male 15 thereby allowing for easy adjustment and selection of latch pawls 20 along latch ridges 21.

Upon the selection of desired position of latch pawls 20, wire 1 is unthreaded and withdrawn from ratchet latch female 14 allowing ratchet latch female 14 to effect its natural molded shape shown in FIG. 4A and creating closed gap GC. The pressure of latch pawls 20 on latch ridges 21 created by the natural closure of ratchet latch female 14 creates a binding and permanent connection and relative positioning between ratchet latch female 14 and ratchet latch male 15.

Figure 5:
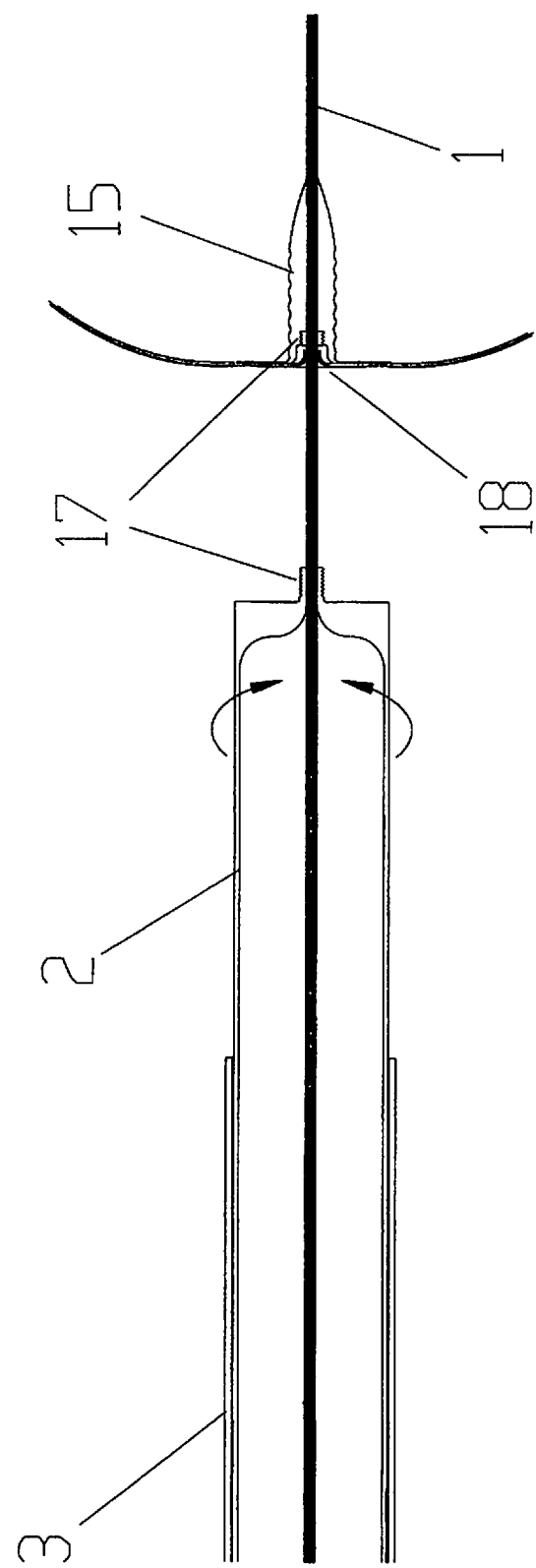
FIGS. 5 and 6 show the ratchet latch male at the predeployment stage.

FIG. 5 illustrates device 19 housed in outer sheath 3 with shell 10 slightly protruding from the head end of outer sheath 3. Protruding shell 10 offers a buffer of highly compliant, low durometer material which allows, during a deployment procedure, incidental inadvertent tissue contact with device 19 without damage to the body tissue.

Figure 6:
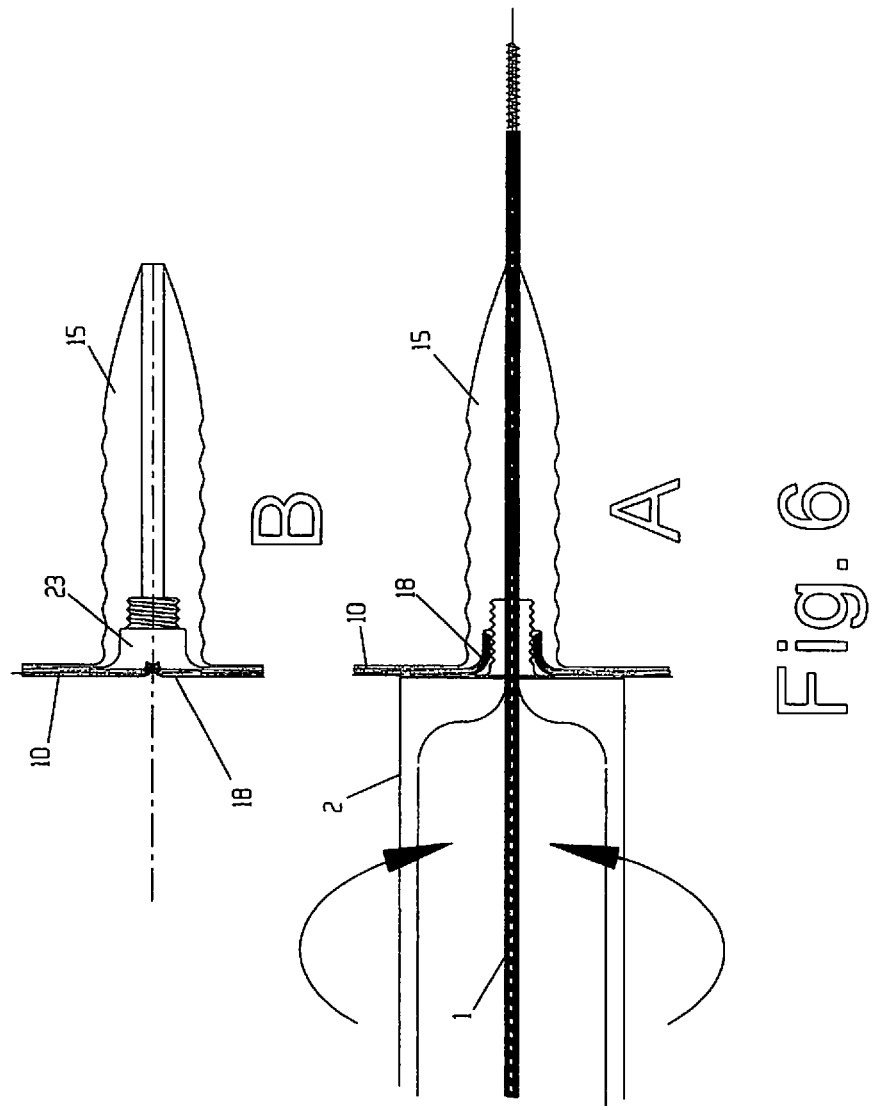

Device 19 configured for pre-deployment assembly in FIG. 6 includes ratchet latch male 15, wire connect threads 16, inner sheath connect threads 17, inner sheath 2, outer sheath 3 and wire 1.

Figure 7:
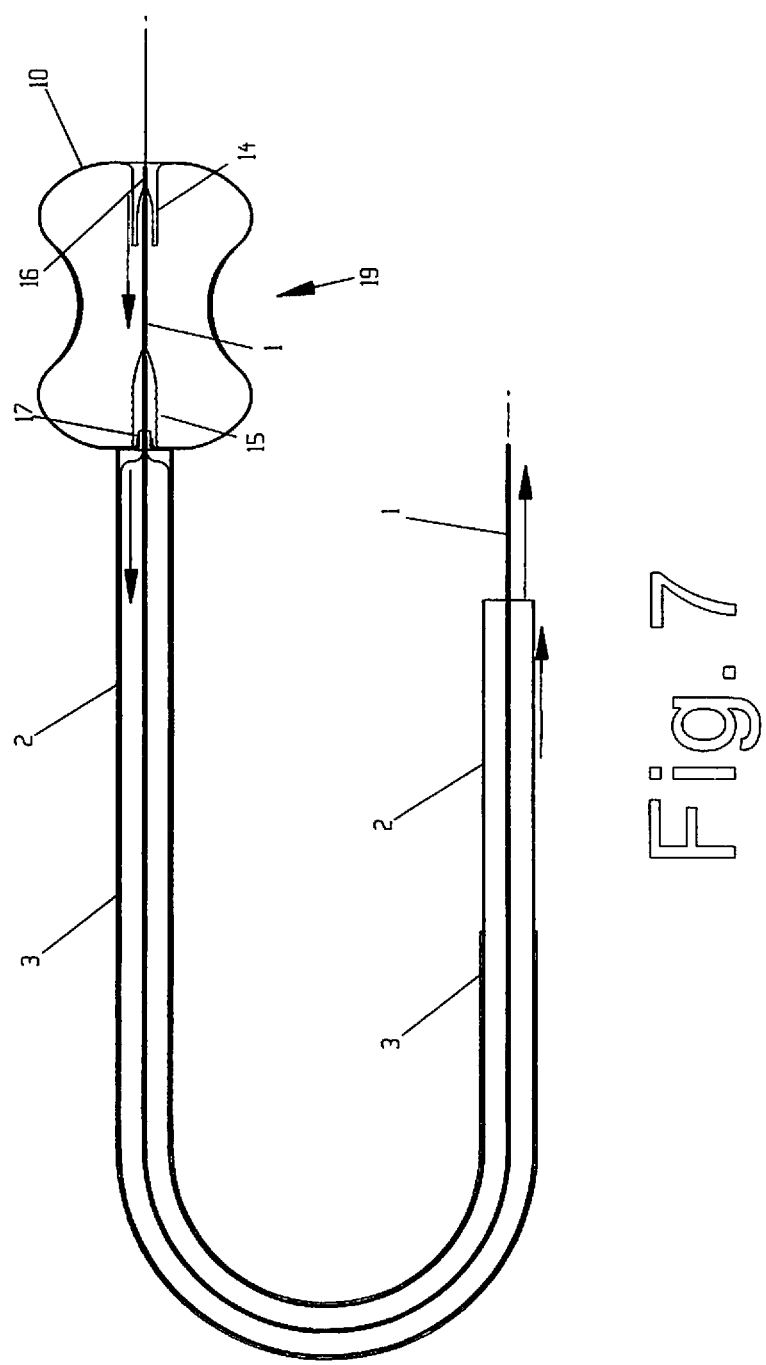
FIGS. 7, 8 and 9 depict further predeployment stages of the device.

FIG. 7 depicts the installation of shell 10 into outer sheath 3. Shell 10, securely attached to inner sheath 2 by inner sheath connect threads 17, is urged to enter the mouth of outer sheath 3 by the manual retraction of inner sheath 2 to cause the travel of shell 10 into outer sheath 3.

Figure 8:
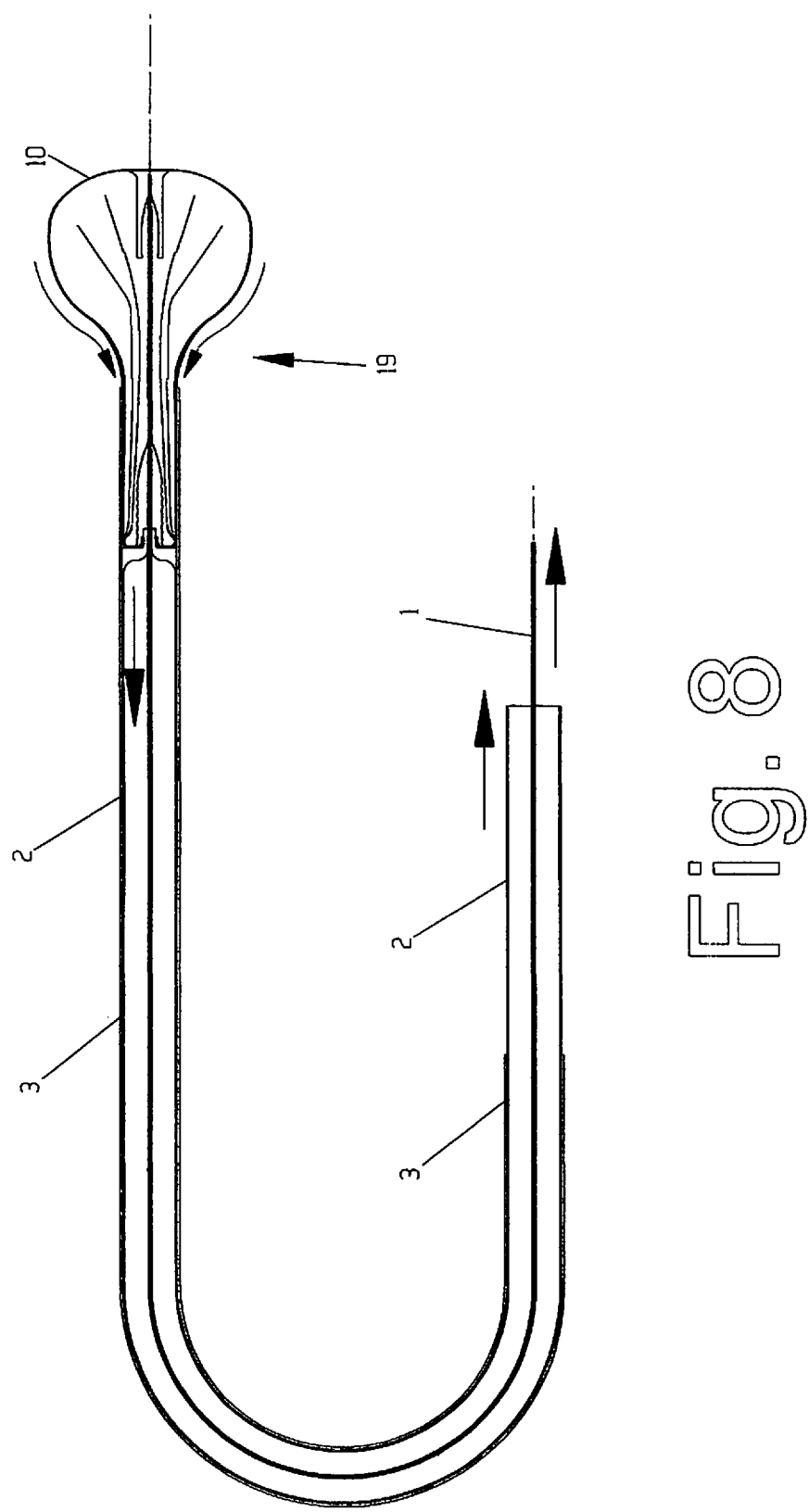

FIG. 8 illustrates the partial installation of shell 10 into outer sheath 3. Shell 10 folds inward on itself as it is urged further into outer sheath 3.

Figure 9:
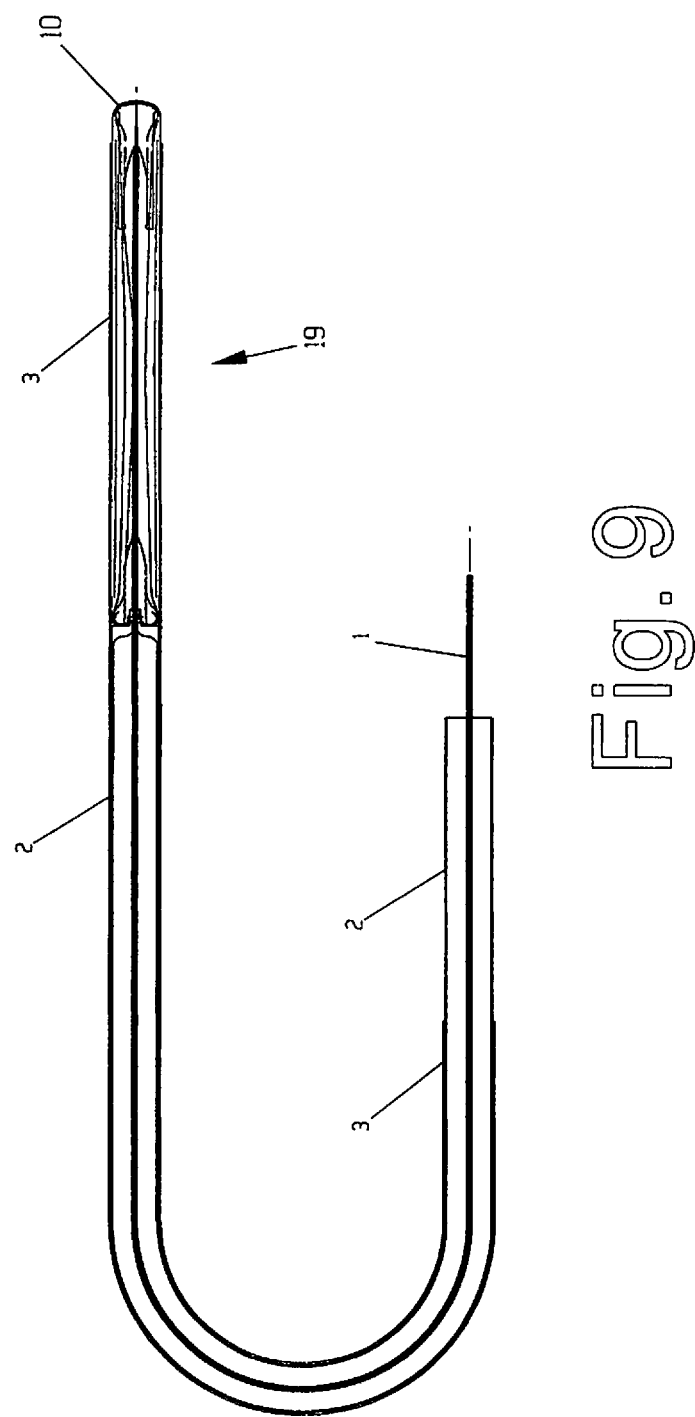

FIG. 9 depicts the complete predeployment installation of shell 10 into outer sheath 3. The installation procedure is stopped short of the total envelopment of shell 10 by outer sheath 3 thereby providing a soft protruding outer bumper to reduce tissue damage by inadvertent contact during deployment.

Figure 10:
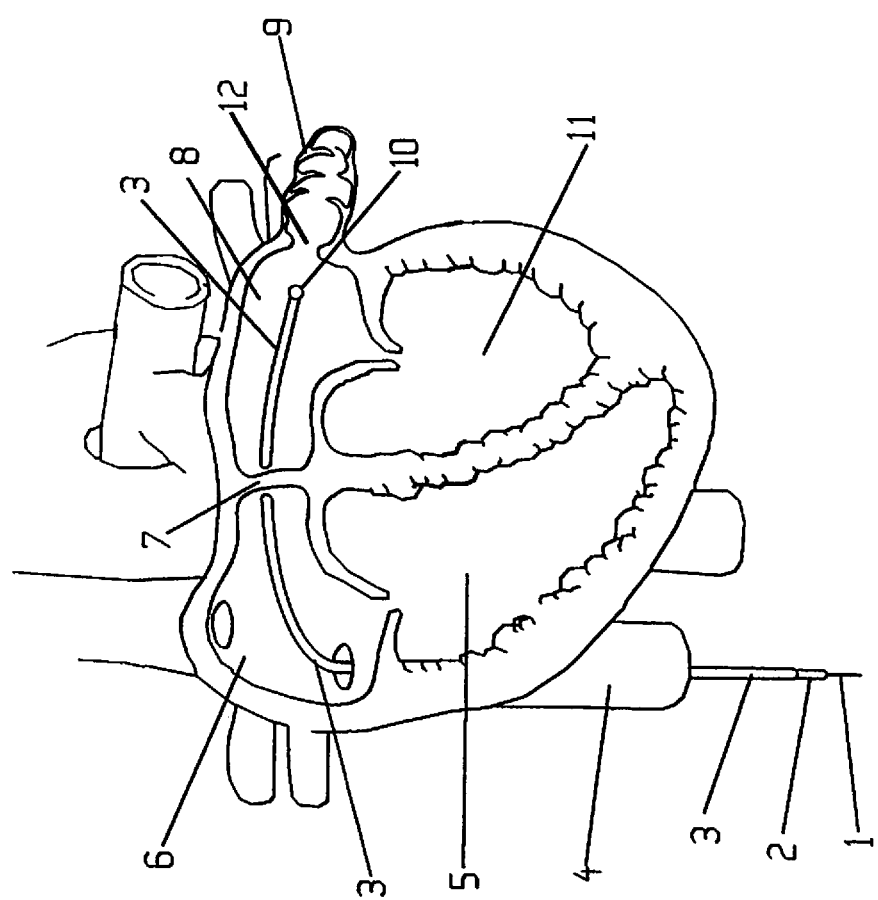
FIGS. 10 and 11 show the device prior to insertion into the LLA orifice.

FIG. 10 shows installation of device 19 in a catheterization setting using standard transseptal procedures. Outer sheath 3 is positioned for deployment of shell 10 with a portion of shell 10 protruding as a bumper to reduce tissue damage by inadvertent contact during the deployment transseptal procedure.

Figure 11:
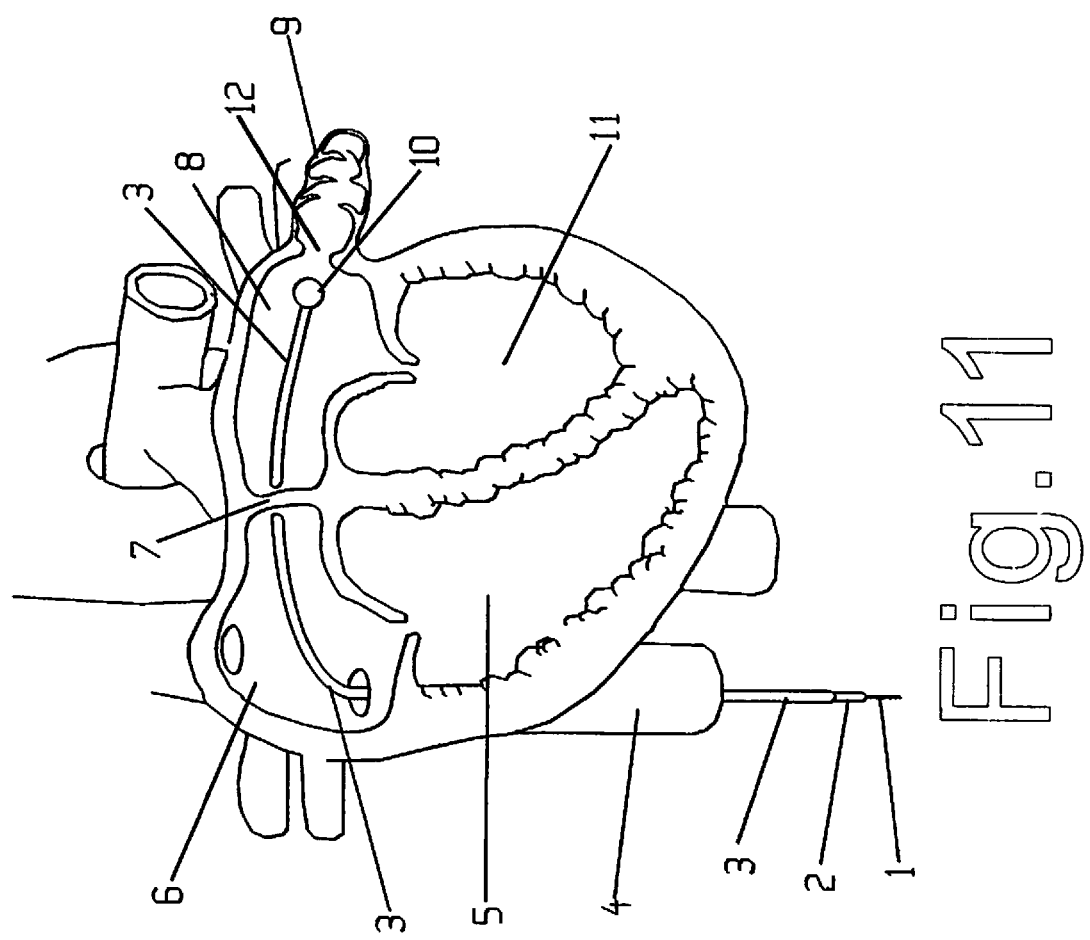

FIG. 11 illustrates the further deployment of shell 10 as it approaches orifice 12 with protruding shell 10 further extended from outer sheath 3 to provide greater protection of tissue from damage by contact during the deployment transseptal procedure.

Figure 12:
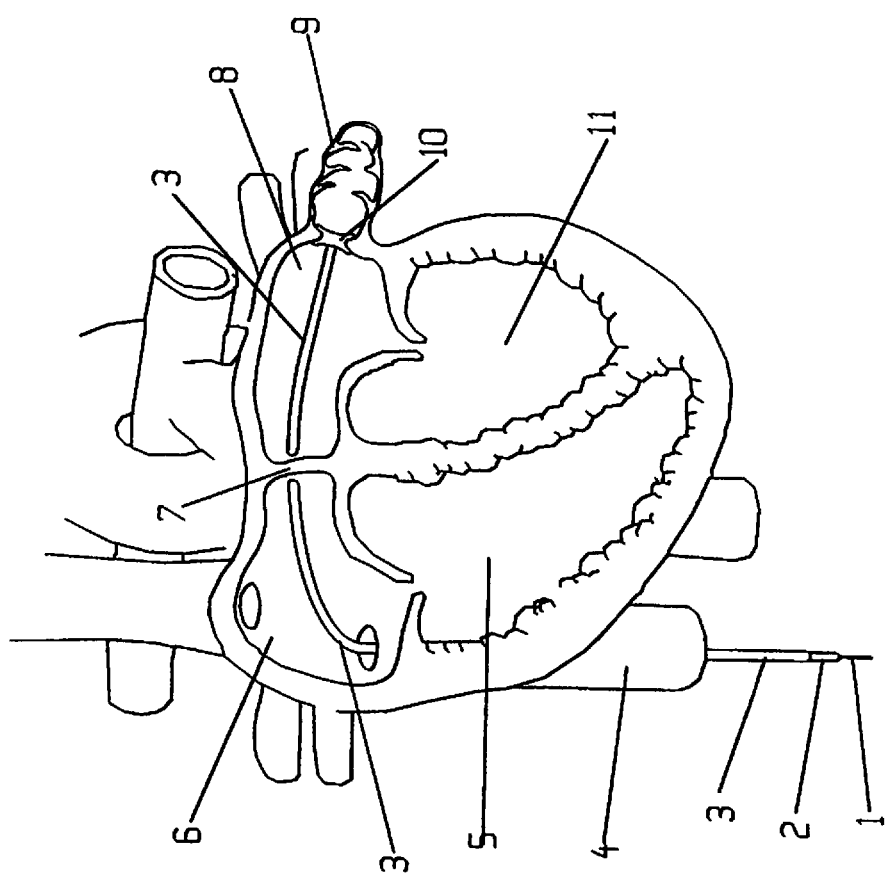
FIGS. 12-18 illustrate the device inserted into the LAA orifice.

FIG. 12 illustrates the closed condition of left atrial appendage 9 with shell 10 in place and secured in orifice 12.

Figure 13:
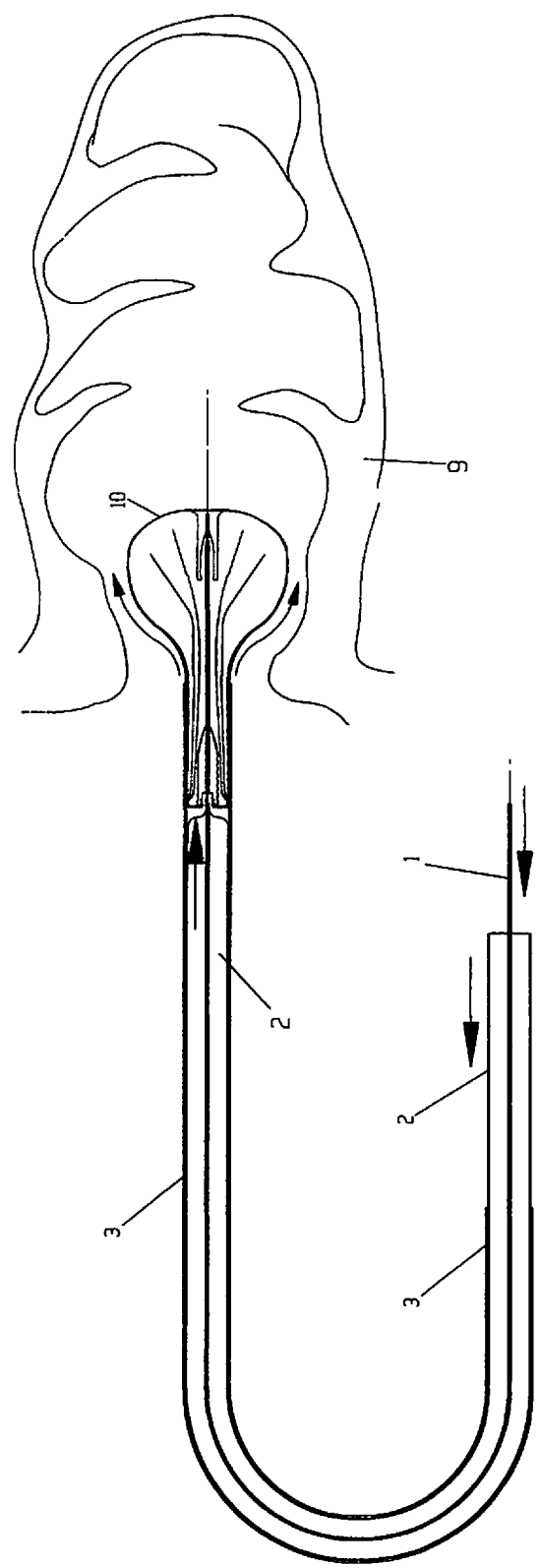

With device 19 deployed in left atrium 9, as shown in FIG. 13, shell 10 is progressively extruded from the mouth of outer sheath 3 by the application of simultaneous and coordinated force on the proximal ends of wire 1 and inner sheath 2. Protruding shell 10, now expanded, offers additional buffering of highly compliant, low durometer material.

Figure 14:
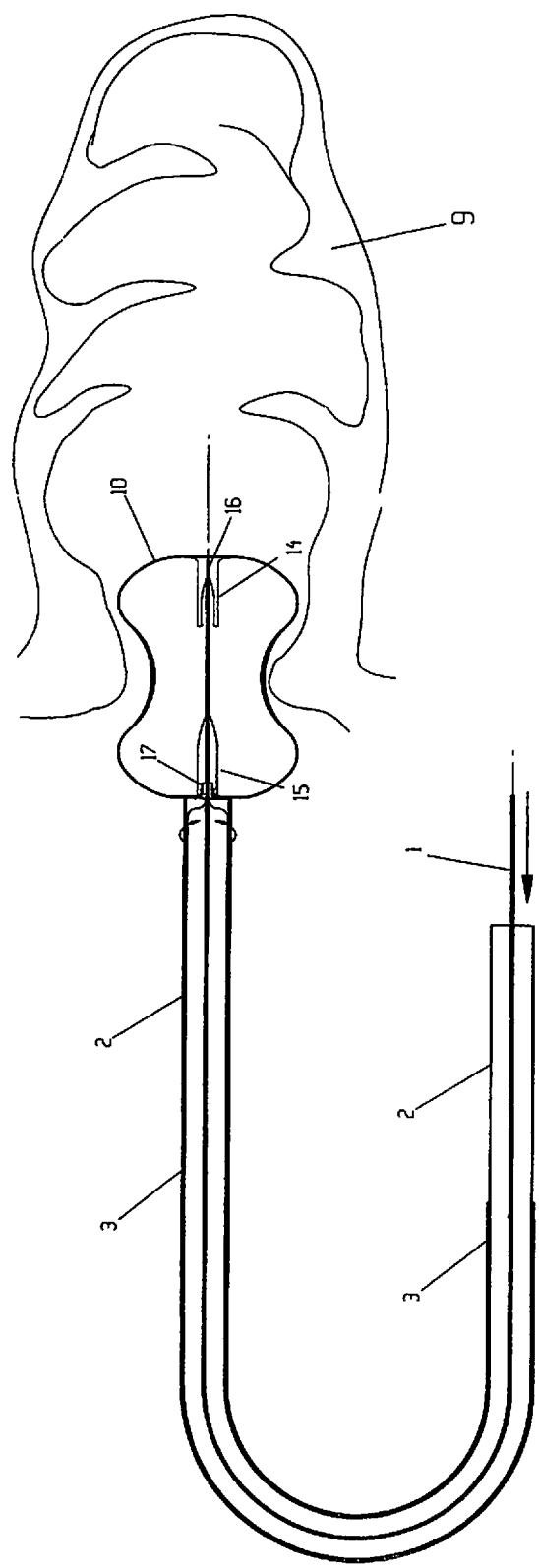

In FIG. 14, device 19 is positioned with its smaller diameter mid-section straddling orifice 12. The opposing larger diameter ends are positioned to secure device 19 in place. Device 19 is therefore fully expelled from outer sheath 3.

Figure 15:
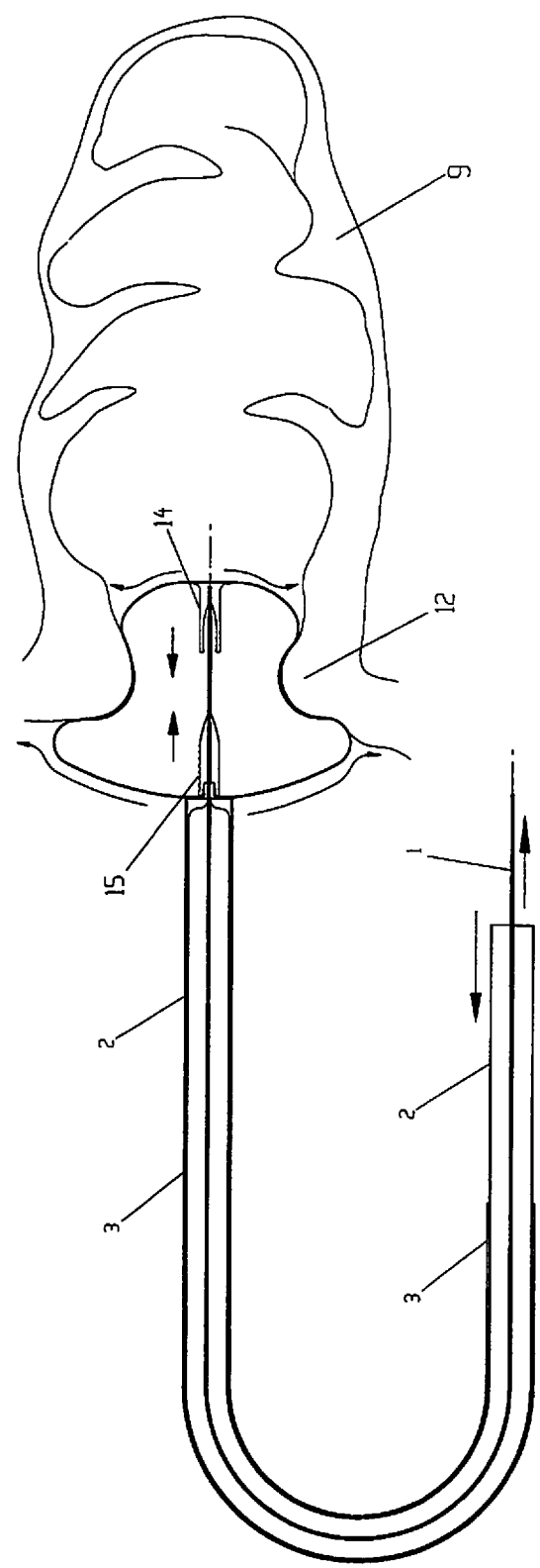

In FIG. 15, shell 10 is positioned with its smaller diameter mid-section deformed to cause intimate contact with orifice 12. The application of an opposing force on wire 1 and inner sheath 2 urges ratchet latch female 14 and ratchet latch male 15 to achieve a connection and causes the opposite larger diameter polar ends of shell 10 to expand with the contact surface area better positioned to secure shell 10 in position in orifice 12.

Figure 16:
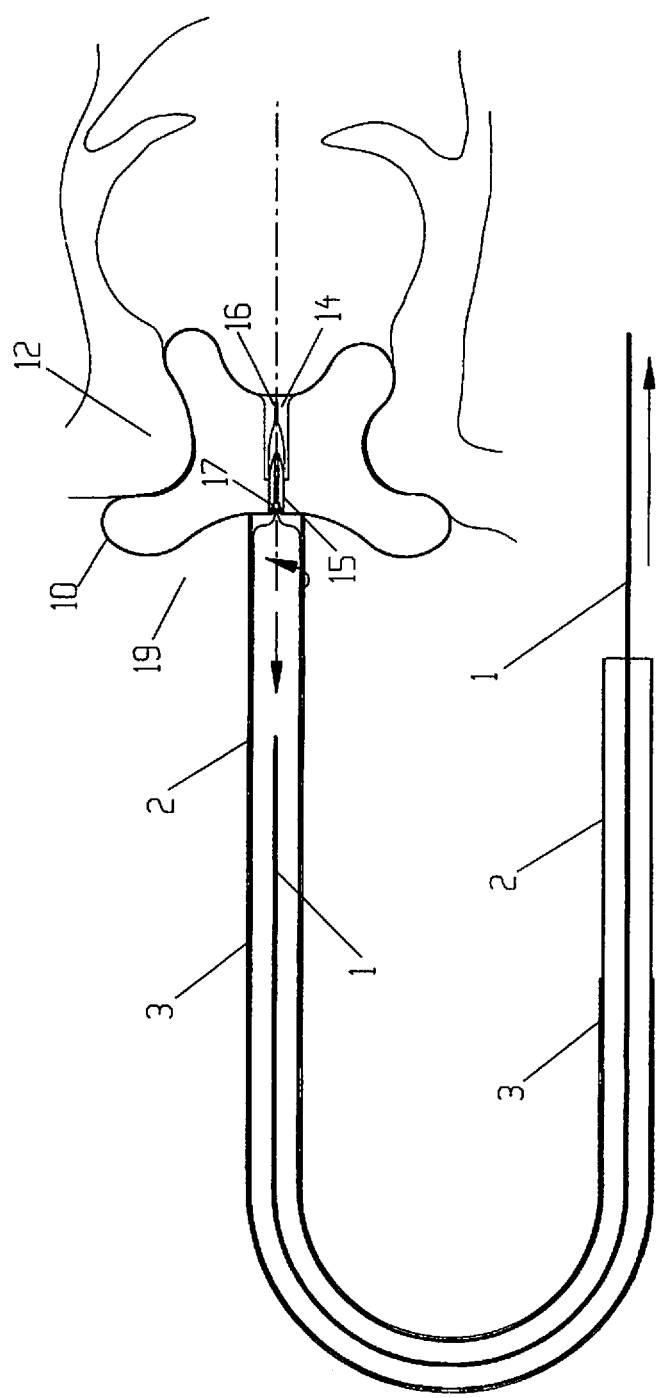

In FIG. 16, shell 10 is fully expanded to contact and conform to the profile of LAA orifice 12. Ratchet latch female 14 and ratchet latch male 15 are engaged at the desired depth for optimum LAA closure. At the desired position of latch pawl 20 on latch ridge 21, wire 1 is unthreaded and withdrawn from ratchet latch female 14 creating a binding and permanent connection and the desired relative position between ratchet latch female 14 and ratchet latch male 15. Inner sheath 2 is then rotated to release inner sheath connect threads 17.

Figure 17:
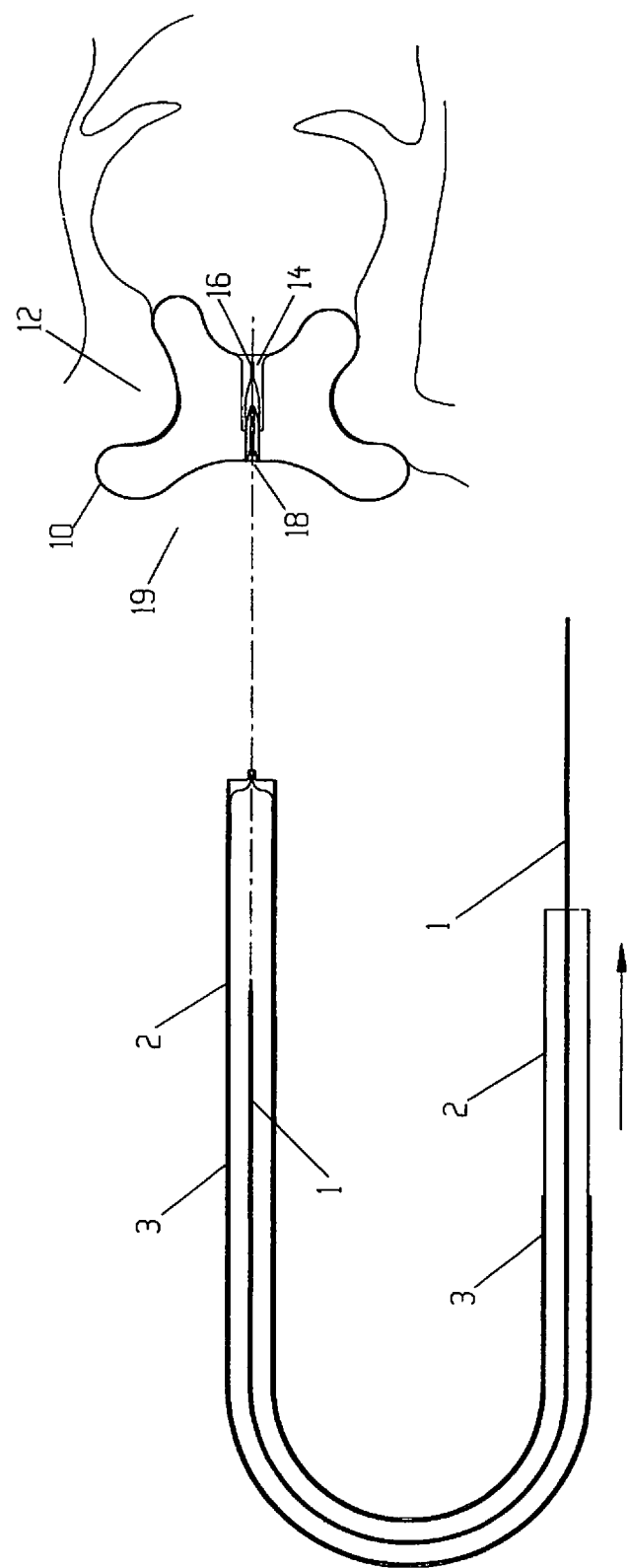

As shown in FIG. 17, device 19 is installed and detached from the deployment system. Close flap 18 has reverted to its original fabricated profile to provide a smooth, consistent textured surface void of cavities and irregularities, as shown in FIG. 6B.

During the deployment process, by monitoring the condition of the patient, progression of the device, variation of patient suitability for deployment at a subsequent stage sequence and other critical and vital factors, it may be decided to abort the deployment and retract the device and all associated transseptal procedure apparatus. The procedure, according to this invention, provides for such retraction at any stage of deployment up to that illustrated in FIG. 16.

Figure 18:
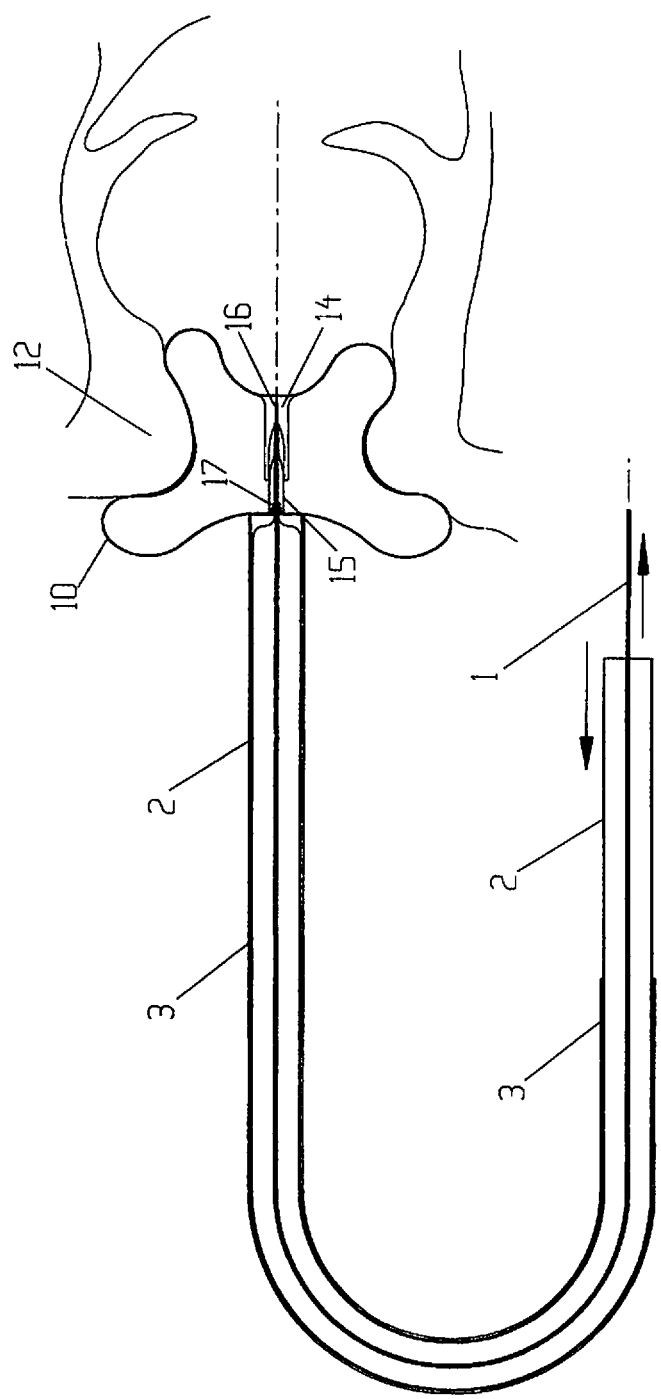

Device 19 can be retracted at any stage of deployment if inner sheath 2 has not been rotated to release inner sheath connect threads 17, as shown in FIG. 18. Wire 1 is inserted and rethreaded in ratchet latch female 14 thereby releasing the binding connection with ratchet latch male 15.

Figure 19:
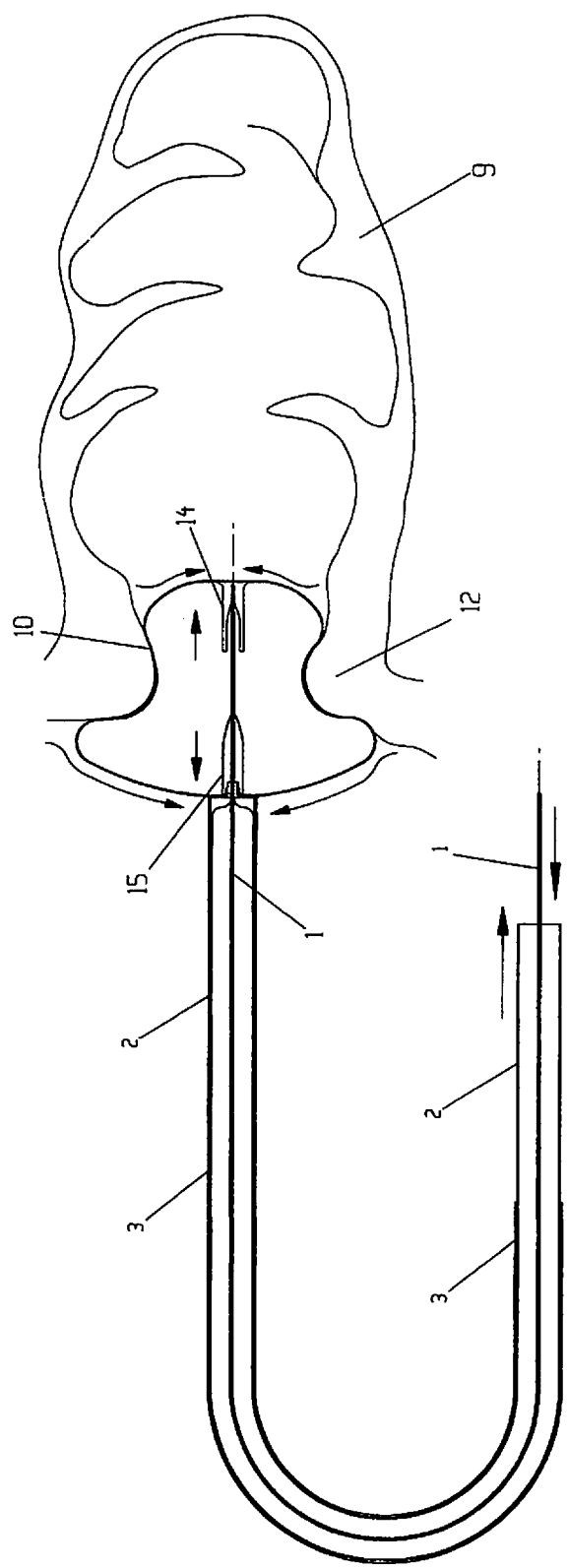
FIGS. 19-21 show withdrawal of the device according to this invention.

In FIG. 19, the release of the closing force between ratchet latch female 14 and ratchet latch male 15 causes shell 10 to extend along its polar axis and retract from contact with orifice 12 and thereby recede and lose contact with surrounding tissue surfaces.

Figure 20:
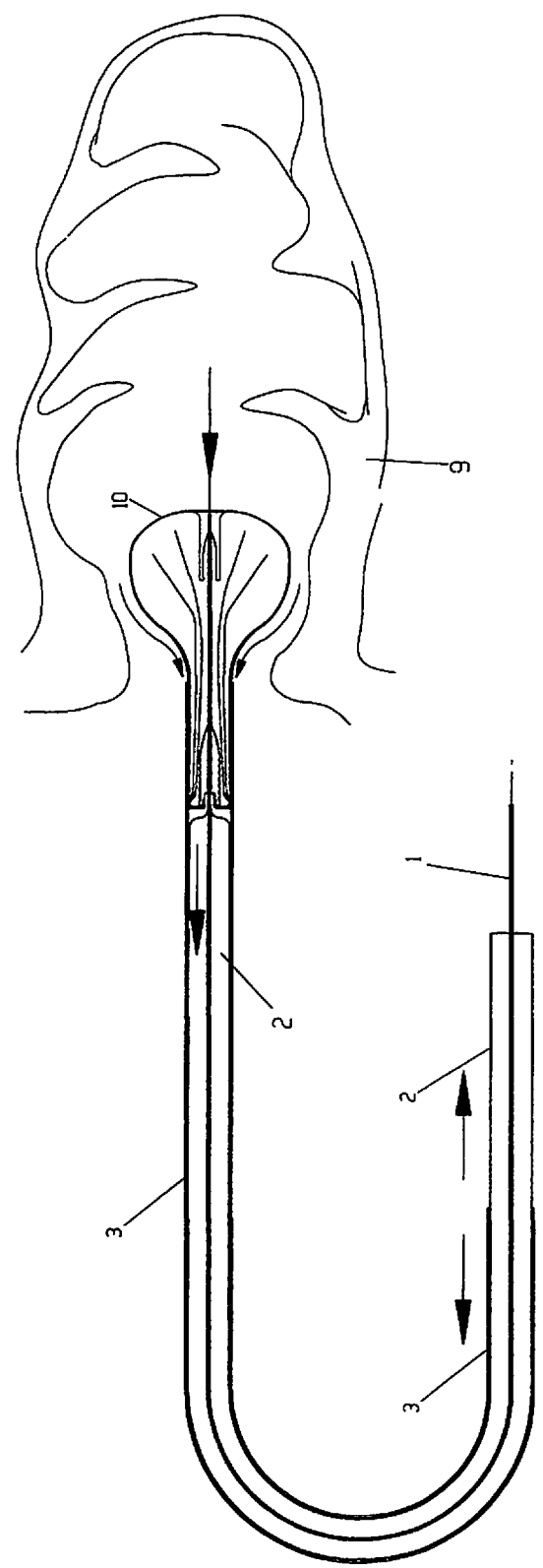

FIG. 20 shows shell 10 progressively recovered into the mouth of outer sheath 3 by application of a simultaneous and coordinated force on the proximate ends of inner sheath 2 and outer sheath 3. If left in place during the extraction procedure, wire 1 is retained in a neutral position where it exerts a negligible force on the operating elements of device 19.

Figure 21:
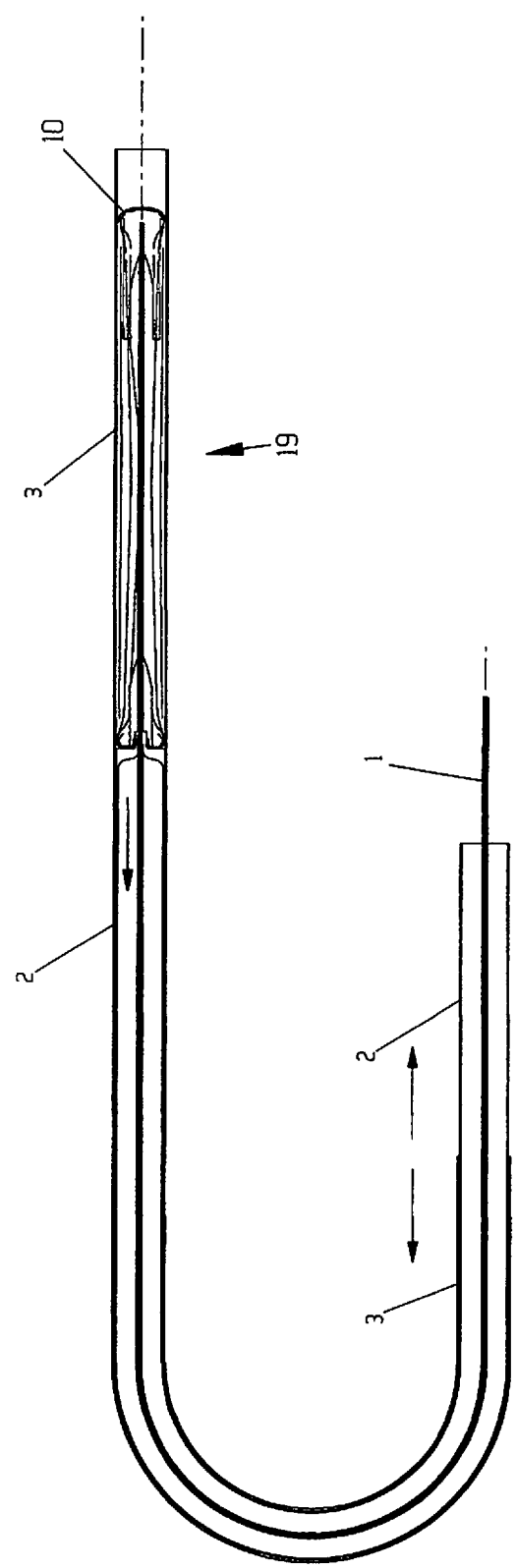

In FIG. 21, device 19 is completely encased in outer sheath 3 and retracted by the pull of inner sheath 2 from the force exerted by the application of simultaneous and coordinated forces on proximate ends of inner sheath 2 and outer sheath 3. If left in place during the extraction procedure, wire 1 is retained in a neutral position where it will exert negligible force on the device's operating elements.

Outer sheath 3 is provided of the correct length and diameter required for the catheterization procedure and encloses inner sheath 2, wire 1 and shell 10. Inner sheath 2 is securely attached to shell 10 by the inner sheath connect threads 17 and wire 1 is securely attached to device 19 by wire connect threads 16.

In operation and during catheterization, outer sheath 3, inner sheath 2 and wire 1 are all manipulated longitudinally and radially by known means such as knobs, finger rings, griping bars and the like disposed at the proximate exposed ends.

The invention claimed is:

1. A device for closing the left atrial appendage comprising:
   a hollow shell having opposite ends,
   a ratchet latch female and a ratchet latch male disposed respectively at said opposite ends,
   said shell inwardly deformable intermediate said opposite ends,
   an outer sheath,
   an inner sheath disposed in said outer sheath,
   said inner sheath directly interconnected to said shell at said male ratchet latch by means of connect threads formed on the end of said inner sheath,
   a wire disposed in said inner sheath,
   the distal end of said wire being threaded,
   said ratchet latch female comprising a threaded slot,
   said threaded end of said wire being receivable in said threaded slot,
   said ratchet latch female comprising latch pawls,
   said ratchet latch male comprising latch ridges formed on the outer periphery thereof and adapted to receive said latch pawls, and
   said latch pawls being biased inwardly to create a natural closing pressure on said latch ridges.

2. The device of claim 1 said shell is constructed from a flexible hybrid elastomer such as a thermoplastic elastomer (TPE).

3. The device of claim 1 wherein said device is constructed by a material additive manufacturing process, including, but not limited to 3-D printing.

4. The device of claim 1 wherein controlled distortion and reshaping of said shell enhances fitting of said device to left atrial appendages having varying orifice diameters and orifice profiles.

5. The device of claim 1 wherein controlled and preselected variation in location and increased thickness of shell wall material at said opposite ends applied during fabrication determines resulting extent and shape of deformation of said shell when a distorting force is applied.

6. The device of claim 5 wherein said shell is provided with a latching and holding means, such means comprising one male and one female member, each member being installed in opposite interior walls along a virtual polar axis of said shell and requiring intimate contact with each other to engage, latch and hold.

7. The device of claim 6 wherein the degree of distortion and reshaping of said shell is controlled by the depth of engagement of said latching and holding means.

8. The device of claim 5 wherein the degree of aggressive latching and holding force is determined by the depth of thread engagement of a thin elongated wire in a threaded system, such force being minimum at full engagement and maximum at full disengagement.

9. The device of claim 1 wherein said shell is provided with a designated virtual polar axis.

10. The device of claim 9 wherein said comprises a thin elongated wire, said wire entering said shell through a hole provided at one pole end of said virtual axis and proceeding along said virtual axis to the opposite interior side wall of said shell for attachment thereto by means of a threaded system.

11. The device of claim 10 wherein extraction of said thin elongated wire from said hole provided in said hollow shell applies collapsing force urging opposite interior side walls of said shell together.

12. The device of claim 1 wherein the surface of said shell is configured with a textured pattern designed to enhance the process of endothelialization.

13. A method of dosing the orifice in the left atrial appendage comprising the steps of:
    encasing a hollow shell in a sheath with said shell comprising a ratchet latch male and an ratchet latch female disposed at opposite ends of said shell,
    an elongated wire disposed in said sheath and said sheath being attached directly to said shell,
    extracting said shell from said sheath,
    positioning said sheath in said orifice,
    manipulating a screw wire to urge said ratchet latch male and said ratchet latch female together,
    the distal end of said wire being threaded,
    said ratchet latch female comprising a threaded slot,
    said threaded end of said wire being receivable in said threaded slot,
    said ratchet latch female comprising latch pawls,
    said ratchet latch male comprising latch ridges formed on the outer periphery thereof and adapted to receive said latch pawls,
    said latch pawls being biased inwardly to create a natural closing pressure on said latch ridges, and
    removing said wire from attachment to said shell.

14. The method of claim 13 wherein during the deployment process, at any point short of final release of device, it is determined to abort the procedure and retract the device and delivery mechanisms, the process is reversed by simple reversal of the steps of the deployment process.

15. The method of claim 13 further comprising the step of passing the leading element of the device through an aperture created in the interatrial septum and entering the left atrium to provide a soft, compliant, bulbous and globular buffer cushion, reducing the probability of damage to body tissue upon contact therewith.

16. The method of claim 13 further comprising the step of sealing said shell at said ratchet latch female.

17. The method of claim 13 further comprising the step of expanding said ends of said shell and reducing the diameter of said shell to secure said shell in said orifice.

* * * * *